United States Patent [19]

Hopp

[11] Patent Number: 4,554,101

[45] Date of Patent: Nov. 19, 1985

[54] IDENTIFICATION AND PREPARATION OF EPITOPES ON ANTIGENS AND ALLERGENS ON THE BASIS OF HYDROPHILICITY

[75] Inventor: Thomas P. Hopp, Seattle, Wash.

[73] Assignee: New York Blood Center, Inc., New York, N.Y.

[21] Appl. No.: 461,802

[22] Filed: Jan. 28, 1983

Related U.S. Application Data

[63] Continuation-in-part of Ser. No. 223,558, Jan. 9, 1981, and a continuation-in-part of Ser. No. 272,855, Jun. 12, 1981, and a continuation-in-part of Ser. No. 358,150, Mar. 15, 1982.

[51] Int. Cl.$^4$ .................. C07C 103/52; C07G 7/00; G01N 33/54; A61K 37/00
[52] U.S. Cl. ..................... 260/112.5 R; 436/543; 514/17; 514/16; 514/15; 514/14; 514/13; 514/12; 514/2; 424/88
[58] Field of Search ............. 260/112.5 R; 435/4, 435/5, 7, 68, 70, 69; 436/518, 543, 547; 424/85, 88

[56] References Cited

U.S. PATENT DOCUMENTS

| | | | |
|---|---|---|---|
| 4,160,019 | 7/1979 | Bjorklund | 436/520 |
| 4,172,827 | 10/1979 | Giaever | 260/112 R |
| 4,196,265 | 4/1980 | Koprowski et al. | 435/2 |
| 4,284,537 | 8/1981 | Beachey | 524/17 |
| 4,415,491 | 12/1983 | Vyas | 260/112.5 R |

FOREIGN PATENT DOCUMENTS

| | | | |
|---|---|---|---|
| 0028563 | 5/1981 | European Pat. Off. | 260/112 R |
| 0044710 | 1/1982 | European Pat. Off. | |
| 0056249 | 7/1982 | European Pat. Off. | |
| 2349569 | 11/1977 | France | |
| 8204250 | 12/1982 | PCT Int'l Appl. | |
| 2045256 | 10/1980 | United Kingdom | 260/112 R |

OTHER PUBLICATIONS

Merrifield, R. B., *Adv. Enzymology*, vol. 32, pp. 221-296.
Rao et al., *Microbios*, vol. 9, pp. 239-245, 1974, "Structure and Activity of Hepatitis B Antigen (HBAg), Studies on Some Non-Functional Aspects and Chemical Modification of Hepatitis B Surface Antigen".
Rose et al., *Proc. Natl. Acad. Sci.*, vol. 77, No. 8, pp. 4643-4647, "Hydrophobic Basis of Packing in Globular Proteins".
Alfred M. Prince et al., "Hepatitis B Virus Vaccine: Identification of HBsAg/d but not HBsAg/y Subtype Antigenic Determinants on a Synthetic Immunogenic Peptide", Proc. Natl. Acad. Sci. USA, vol. 79, No. 2, Jan. 1982, pp. 579-582, Immunology.
Pradip K. Bhatnagar et al., "Immune Response to Synthetic Peptide Analogues of Hepatitis B Surface Antigen Specific for the A Determinant", Proc. Natl. Acad. Sci. USA, vol. 79, No. 14, Jul. 1982, pp. 4400-4404, Immunology.
"La Jolla Biologists Troubled by the Midas Touch", Science, vol. 213, Aug. 7, 1981, pp. 623-628.
Pierre Tiollais, Patrick Charnay, Girish N. Vyas, "Biology of Hepatitis B Virus", Science, vol. 213, Jul. 24, 1981, pp. 406-411.
Atsuhiko Machida et al., "A Glycopeptide Containing 15 Amino Acids Residues Derived from Hepatitis B Surface Antigen Particles: Demonstration of Immunogenecity to Raise Anti-HBs In Mice", Molecular Immunology, vol. 19, No. 9, 1982, pp. 1087-1093.
Ruth Arnon, "Anti-Viral Activity Induced by Synthetic Peptides Corresponding to Regions Involved in Viral Neutralization", Pharmac. Ther., vol. 6, 1979, pp. 275-289.
Francoise Audibert et al., "Augmentation de la Response Immunitaire au Vaccine Grippal par un Glycopeptide Synthetique Adjuvant", Seanes Acad. Sci., Ser. D, t. 285, Sep. 12, 1977, pp. 267-270.
F. Audibert et al., "Active Antitoxic Immunization by a Diphtheria Toxin Synthetic Oligopeptide", Nature, vol. 289, No. 5798, Feb. 12, 1981, pp. 593-594.
Chemical Abstracts, vol. 92, No. 5, Feb. 4, 1980, p. 587, No. 39507v, R. Arnon et al.
Chemical Abstracts, vol. 95, No. 18, Nov. 2, 1981, p. 367, No. 156407k, Sela et al.
Chemical Abstracts, vol. 88, No. 1, Jan. 2, 1978, p. 410, No. 4589p, Audibert et al.
Tom Hopp, "The Immunochemistry of α-Lactalbumin", Ph.D. Thesis Proposal-Cornell University Graduate School of Medical Sciences, Sep. 1974.
Thomas P. Hopp and Kenneth Woods, "Prediction of Protein Antigenic Determinants from Amino Acid Sequences", Proc. Natl. Acad. Sci-USA, vol. 78, No. 6, pp. 3824-3828, Jun. 1981.
Thomas P. Hopp, "A Synthetic Peptide with Hepatitus B Surface Antigen Reactivity," Molecular Immunology, vol. 18, No. 9, pp. 869-872, 1981.

(List continued on next page.)

*Primary Examiner*—Thomas G. Wiseman
*Assistant Examiner*—Robin Lyn Teskin
*Attorney, Agent, or Firm*—Sprung Horn Kramer & Woods

[57] ABSTRACT

An immunoglobulin is provided which consists essentially of a mono-specific, hetero-molecular antibody which is mono-specific to a single antigenic or allergenic determinant. The antibody is specific to the H-epitope of a protein antigen or allergen. The H-epitope is defined by a sequence of at least six amino acids corresponding to the sequence of such amino acids in the protein antigen or allergen where the greatest local average hydrophilicity of the protein antigen or allergen is found.

6 Claims, No Drawings

OTHER PUBLICATIONS

Gernut Walter et al., "Antibodies Specific for the Carboxy and Amino-Terminal Regions of Simian Virus 40 Large Tumor Antigen", Proc. Natl. Acad. Sci. USA, 77, Sep. 1980, pp. 5197-5200.

J. G. Sutcliffe et al., "Chemical Synthesis of a Polypeptide Predicted from Nucleotide Sequence Allows Detection of a New Retroviral Gene Product", Nature, vol. 187, Oct. 1980, pp. 801-805.

M. Z. Atassi, "Antigenic Structure of Myoglobin: The Complete Immunochemical Anatomy of A Protein and Conclusions Relating to Antigenic Structures of Proteins", Immunochemistry, vol. 12, 1975, pp. 423-438.

Chemical Abstracts, 89:177673k, 1978.

Chemical Abstracts, 90:136014y, 1978.

Chemical Abstracts, 88:87441h, 1977.

Synthetic Peptides for Molecular Biology Brochure, Cambridge Research Biochemicals (6 pages), 1984.

IDENTIFICATION AND PREPARATION OF EPITOPES ON ANTIGENS AND ALLERGENS ON THE BASIS OF HYDROPHILICITY

CROSS REFERENCE TO RELATED APPLICATIONS

This is a continuation-in-part of each of copending applications Ser. No. 223,558 filed Jan. 9, 1981; Ser. No. 272,855 filed June 12, 1981 and Ser. No. 358,150 filed Mar. 15, 1982; assigned to the assignee hereof, the disclosures of which are hereby specifically incorporated herein by reference.

BACKGROUND OF THE INVENTION

Field of the Invention

This invention relates to immunoglobulins containing mono-specific, hetero-molecular antibodies which are mono-specific to an antigenic or allergenic determinant of a particular antigen or allergen. This invention also relates to a method of determining the antigenic or allergenic determinants of protein antigens or allergens on the basis of the determination of the point of greatest local average hydrophilicity of such protein antigens or allergens. Furthermore, this invention concerns forming a synthetic peptide containing a designated sequence of six amino acids chains corresponding to the point of greatest local average hydrophilicity. The present invention also relates to the use of such mono-specific, hetero-molecular antibodies in diagnostic test kits and in the detection of the presence of antigens.

DISCUSSION OF RELATED APPLICATIONS

In my co-pending applications referred to above, I disclosed a new system for determining that portion of the protein of a natural antigen or allergen which is responsible for the antigenicity or allergenicity of the protein. More especially I defined a process for determining the specific sequences of amino acid of proteinaceous allergens or antigens which are causative of an immune response when compositions containing the same are injected into host animals.

Thus I disclose not only that method for determining the specific sequence of amino acids but a method of preparing synthetic antigens or allergens knowing the precise number and sequence of amino acids which must be present. I also disclose numerous synthetic vaccines comprising a short polypeptide supported on a carrier, the carrier considered to be of critical importance in providing the active portion of the synthetic peptide chain with sufficient size so that the entire synthetic antigen or synthetic allergen can be recognized by the immune system and evoke formation of the corresponding antibodies.

Specifically, my synthetic vaccine comprises a physiologically acceptable carrier in or on which is disposed a synthetic peptide residue containing a sequence of at least six amino acids corresponding to the sequence of such amino acids in a protein antigen or allergen with the greatest local average hydrophilicity of the antigen or allergen, said local hydrophilicity of said protein antigen or allergen being defined by and determined by:

A. assigning relative hydrophilicity values to the amino acids of the protein antigen or allergen in accordance with relative relationship of such amino acids as shown in the table below:

| Amino Acid | Hydrophilicity Value |
|---|---|
| Arginine | 3.0 |
| Aspartic Acid | 3.0 ± 1 |
| Glutamic Acid | 3.0 ± 1 |
| Lysine | 3.0 |
| Serine | 0.3 |
| Asparagine | 0.2 |
| Glutamine | 0.2 |
| Glycine | 0.0 |
| Proline | −0.5 ± 1 |
| Threonine | −0.4 |
| Alanine | −0.5 |
| Histidine | −0.5 |
| Cysteine | −1.0 |
| Methionine | −1.3 |
| Valine | −1.5 |
| Isoleucine | −1.8 |
| Leucine | −1.8 |
| Tyrosine | −2.3 |
| Phenylalaine | −2.5 |
| Tryptophan | −3.4 |

B. determining the repetitive local average of hydrophilicity values at a plurality of points along the amino acid sequence; and C. determining from such local points of repetitive averages the points of greatest local average hydrophilicity; said composition being characterized by evoking a protective immunological response or by stimulation of antibody formation or decreased sensitivity to allergen when introduced into a host animal in the absence of the entire amino acid sequence of the protein antigen or allergen.

At the heart of the development there is the determination of a sequence of six amino acids which are critical to the production of the immunological response. In accordance with such earlier invention this is done with the foreknowledge of the amino acid sequence of an antigen or allergen, but if the same is unknown, then the amino acid sequence of the entire protein must first be determined. This can be done by known but laborious means.

Given the amino acid sequence of the entire protein antigen or allergen, the next objective is to determine the point along said molecule where there is greatest local average hydrophilicity. This is initially done by assigning relative hydrophilicty values in accordance with the table above to each amino acid in the protein. Thereafter, those values are repetitively averaged along the length of the protein. While such method is successful when averaging groups ranging in size from four to ten successively connected amino acids, it is preferred that in determining such local averages the hydrophilicity values of five to seven linearly connected amino acids be employed, especially six such amino acids. At a plurality of points along the amino acid chain of the protein, the local averages are determined (moving average, increment of one).

Once the repetitive local average of the specific hydrophilicity values are determined, the precise point of greatest hydrophilicity can be easily located by inspection or determined graphically or otherwise. Furthermore, the precise point of the second greatest hydrophilicity, the third greatest hydrophilicity and so on can also be located. It has been discovered that the six amino acids providing the greatest local average hydrophilicity are the sequence of six amino acids which are critical to the production of the immunological response. Stated differently, it has been found that this sequence of six amino acids is present in an epitope (antigenic determinant) of the protein, i.e. the sequence of amino acids recognized by and bound by an antibody with immunological specificity. Such epitope, is hereinafter designated as the "H-epitope" as it is the epitope of greatest local average hydrophilicity.

With this realization of the precise sequence of amino acids which accounts for H-epitope of a given protein antigen or allergen, one can form a synthetic vaccine in any number of ways.

The synthetic vaccine is prepared either by chemically synthesizing a chain of amino acids corresponding to the sequence of amino acids of the H-epitope or the H-epitope is obtained from a protein containing the same by selective lysis such as by splitting the protein by the use of enzymes. The amino acid chain containing the H-epitope so obtained either synthetically or from naturally occurring protein is thereafter disposed on a physiologically acceptable carrier, and the resultant composition is thereafter diluted with physiologically acceptable medium. The composition is then ready for introduction into a host animal.

It will be realized that the aforementioned development is useful in the formation of synthetic vaccines of known and unknown, identified or unidentified, protein antigens or allergens, since the focus is upon the portion of the protein molecule which provides the H-epitope. Thus, the synthetic vaccine of the aforementioned development can contain H-epitopes of single or multiple known or unknown protein antigens or allergens. The synthetic vaccine can contain a plurality of H-epitopes of a single antigen or can contain a single H-epitope of a first antigen and an H-epitope of a second antigen or allergen. The synthetic vaccine can contain one or more epitopes of an antigen or allergen alone or in combination with one or more epitopes of a second antigen or allergen. In fact, the synthetic vaccine can contain as many epitopes corresponding to said sequence of six amino acids of greatest local average hydrophilicity as desired, and said epitopes can correspond to the sequence of six amino acids from a wide variety of antigens or allergens. The vaccine contains at least one epitope. This epitope can be co-present with other epitopes of the same or different antigens which are not H-epitopes, i.e., do not correspond to the point of greatest local average hydrophilicity of the antigen or allergen.

The process of the aforementioned development is useful in the formation of synthetic vaccines from antigens whose amino acid sequence has not heretofore been reported. The art well knows how to determine the amino acid sequence of a protein antigen or allergen. It remains, therefore, a simple matter in accordance with the aforementioned development to determine the H-epitope.

The synthetic vaccine can have H-epitopes of any protein antigen or allergen. The vaccine of the following protein antigens or allergens are particularly contemplated. Hepatitis B surface antigen, histocompatibility antigens, influenza hemaglutinin, fowl plague virus hemagglutinin, rag weed allergens Ra3 and Ra5 and the antigens of the following viruses: vaccinia, Epstein-Barr virus, polio, rubella, cytomegalovirus, small pox, herpes, simplex types I and II, yellow fever, and many others.

It can also alternatively or additionally have an H-epitope of a protein of any of the following parasites: organisms carrying malaria (P. Falciporum, P. Ovace, etc.). Schistosomiasis, Onchocerca Volvulus and other filiarial parasites, Tyrpanosomes, Leishmania, Chagas disease, amoebiasis, hookworm, and the like. In addition, vaccines of the following bacteria are especially contemplated: leprosy, tuberculosis, syphilis, gonorrhea and the like.

Vaccines of the following viruses can be made by the process of the aforementioned development: Infectious ectromelia virus, Cowpox virus, Herpes simples virus, Infectious bovine rhinotracheitis virus, Equine rhinopneumonitis (equine abortion) virus, Malignant catarrh virus of cattle, Feline rhinotracheitis virus, Canine herpesvirus, Epstein-Barr virus (ass. with infectious mononucleosis and Burkitt lymphoma), Marek's disease virus, Sheep pulmonary adenomatosis (Jaagziekle) virus, Cytomegaloviruses, Adenovirus group, Human papilloma virus, Feline panleucopaenia virus, Mink enteritis virus, African horse sickness virus (9 serotypes), Blue tongue virus (12 serotypes), Infectious pancreatic necrosis virus of trout, Fowl sarcoma virus (various strains), Avian leukosis virus, visceral, Avian leukosis virus, erythroblastic, Avian leukosis virus, myeloblastic, Osteopetrosis virus, Newcastle disease virus, Parainfluenza virus 1, Parainfluenza virus 2. Parainfluenza virus 3, Parainfluenza virus 4, Mumps virus, Turkey virus, CANADA/58, Canine distemper virus, Measles virus, Respiratory syncytial virus, Myxovirus, Type A viruses such as Human influenza viruses, e.g. Ao/PR8/34, Al/CAM/46, and A2/Singapore/1/57; Fowl plague virus; Type B viruses e.g. B/Lee/40; Rabies virus; Eastern equinine encephalitis virus; Venezuelan equine encephalitis virus; Western equine encephalitis virus; Yellow fever virus, Dengue type 1 virus (=type 6), Dengue type 2 virus (=type 5); Dengue type 3 virus; Dengue type 4 virus; Japanese encephalitis virus, Kyasanur Forest virus; Louping ill virus, Murray Valley encephalitis virus; Omsk haemorrhagic fever virus (types 1 and 11); St. Louis encephalitis virus; Human rhinoviruses, Foot-and-mouth disease virus; Poliovirus type 1; Enterovirus Polio 2; Enterovirus Polio 3; Avian infectious bronchitis virus; Human respiratory virus; Transmissible gastro-enteritis virus of swine; Lymphocytic choriomeningitis virus, Lassa virus; Machupo virus; Pichinde virus; Tacaribe virus; Papillomavirus.

Similarly, the synthetic vaccine can have an H-epitope of any protein allergen such as the rag weed allergens.

It is to be understood that the foregoing lists are not all-inclusive, but simply exemplary, since the heart of the aforementioned development resides in reliably and confidently predicting and determining the H-epitope.

In forming a synthetic vaccine according to the earlier invention, it is preferred to insure that the epitope has the steric configuration to be recognized by an antibody; that the given sequence of 6 amino acids have bonded thereto as part of the amino acid chain at least three amino acids on either side thereof, these three adjacent amino acids serving as auxiliary acids to insure the stabilization of the epitope so that it is readily recognized by and neutralized by an antibody.

In one of its simplest forms, that invention comprises a physiologically acceptable carrier on which is disposed a synthetic peptide residue of the designated epitope. This synthetic peptide residue has a chain length of minimally six amino acids, preferably twelve amino acids (considering the three amino acids on either side thereof) and can contain an infinitely long chain of amino acids or their components, which can be characterized by the presence of other epitopes of the same or different antigen or allergen. Where it is free of such additional chain with or without such additional eptitopes, it generally does not have an amino acid chain exceeding 50 amino acids. Where a short chain is desired containing the desired epitope, it preferably does not have an amino acid chain length greater than 40, more especially not greater than 30 and more particularly not greater than 20 amino acids. Optimally the peptide residue has an amino acid chain length of 12 to 18 amino acids, preferably 12 to 15 amino acids, especially 12 amino acids.

Where, however, the epitope is part of a long chain, such as when there are more than one epitopes on the chain, the chain can contain residues of any of the following moieties; segments of polyamino acid, polysaccharides, polyamides, vinyl polymers, ester polymers, polyacetals, polyolefins, polyphenyl sulfide, polycarbonates as well as bivalent organo radicals, including bivalent alkylene and other saturated or unsaturated organo e.g. hydrocarbon radicals. These residues can have molecular weights of up to 1,000,000, preferably between 10,000 and 100,000, the molecular weight being determined by ultracentrifugation. If the chain comprises an amino acid chain, the chain preferably comprises no more than 2,000 amino acids, excluding amino acids associated with an epitope.

It will be realized that a chain containing the basic sequence of the H-epitope can contain a vaccine adjuvant. Such vaccine adjuvants include muramyl dipeptide and analogs which can be covalently bonded.

Alternativly, the vaccine can comprise a chain of amino acids containing one or more H-epitopes together with other chains of amino acids forming epitopes of the same antigen or allergen or of different antigens or allergens. These additional chains can be of the same or different chain length. The chains which contain epitopes can be interconnected with one another such as by crosslinking or by being bonded directly thereto in the form of a branched chain, or the respective chains are bonded to a central "carrier". Where there is a plurality of epitope containing chains, a given epitope chain can contain a chain adjacent the epitope of molecular weight up to 1,000,000, determined in accordance with the foregoing method, which chain can serve as a bridge to other epitopes, it being realized that these other epitopes can be epitopes of the same allergen or antigen as the epitope in the chain, the same epitope as the epitope of the antigen or allergen in another chain, or can be a third, fourth or fifth, etc., epitope, as the case may be. It is contemplated that the vaccine contain a plurality of the same or different epitopes. In particular, it is contemplated that a vaccine contain between 1 and 1,000 epitopes, of the same antigen or allergen per covalent unit. It can also have present in addition thereto between 1 and 1,000 epitopes per covalent unit of a different antigen or allergen or plurality of different antigens or allergens, all as desired.

The H-epitope requires proper presentation in order to elicit an immune response. To this end, a carrier may be provided for such H-epitopes. It should be understood, however, that a carrier may not be required to practice the present invention, i.e., a carrier may not be required to produce immunoglobulins according to the present invention. The "carrier" is simply a physiologically acceptable mass to which the H-epitopes is attached. A carrier can comprise simply a chain of amino acids or other moieties and to that end it is specifically contemplated to use as a carrier a dimer, oligomer, or higher molecular weight polymer of sequences containing the six amino acids. In other words, having determined which sequence of six amino acids forms the H-epitope, these amino acids can be formed from naturally available materials or synthetically and can be polymerized to build up a chain of two or more repeating units so that repeating sequences serves both as "carrier" and H-epitopes. Stated differently, an independent carrier is not required. It is preferred that alternative carriers comprise some substance, animal, vegetable or mineral, which is physiologically acceptable and functions to present the H-epitope so that it is recognized by the immune system of a host and stimulates a satisfactory immunological response. Thus, a wide variety of carriers are contemplated, and these include materials which are inert, which have biological activity and/or promote an immunological response. For instance, proteins can be used as carriers and there is included within such subclass hemoglobin, human serum proteins, tetanus toxoid.

Polysaccharides are also contemplated as carriers, and these include especially those of molecular weight 10,000 to 1,000,000, including in particular starches, dextran, agarose, ficoll or its carboxy methyl derivative and carboxy methyl cellulose.

Polyamino acids are also contemplated for use as carriers, and these polyamino acids include, among others, polylysine, polyalanyl polylysine, polyglutamic acid, polyaspartic acid and poly ($C_2$–$C_{10}$) amino acids.

Vaccines can be used as carriers for the epitopes provided by the invention. In other words, the synthetic or naturally derived peptide residues provided by the invention can themselves be attached to other vaccines including vaccines for measles, influenza, smallpox, polio, diphtheria, pneumonococci, meningococci, as well as the vaccines of the virus and organisms mentioned above.

The carrier can conveniently be a living organism such as bacteria.

Organic polymers can be used as carriers, and these polymers include polymers and copolymers of amines, amides, olefins, vinyls, esters, acetal, polyamides, carbonates, ethers, phenylene sulfides, silicones, urea formaldehyde condensation products, phenol formaldehyde condensation products, urethanes, melamine formaldehydes, epoxy resins, acrylic resins, allyl resins, and the like. Generally speaking, the molecular weight of these polymers will vary dramatically. The polymers can have from two repeating units up to several thousand e.g., two thousand repeating units. Of course, the number of repeating units will be consistent with the use of the vaccine in a host animal. Generally speaking, such polymers will have a lower molecular weight, say between 10,000 and 100,000, determined in accordance with the procedure set forth above.

Inorganic polymers can also be employed. These inorganic polymers can be inorganic polymers containing organo moieties. In particular, silicates can be used as carriers. It is preferred that the carrier be one which is an immunological adjuvant. In such cases, it is particularly contemplated that the adjuvant be any one of the following: muramyl dipeptide or its analogs.

The carrier can also be the residue of a crosslinking agent employed to interconnect a plurality of epitope-containing chains. The crosslinking agent can be one which interconnects the chains at a point containing the sequence of six amino acids. Alternatively, the crosslinking agent can interconnect a plurality of chains at a point other than where the epitope is formed. Crosslinking agents which are contemplated include crosslinking agents which have as their functional group an aldehyde, carboxyl, amine, amido, imido or azidophenyl, group. In particular, there is contemplated the use of butyraldehyde as a crosslinking agent, a divalent imido ester or a carbodiimide. Particularly contemplated divalent imido esters are those of the formula

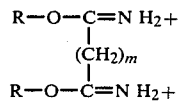

wherein m is 1 to 13 and R is an alkyl group of 1 to 4 carbon atoms.

Particularly contemplated carbodiimides for use as crosslinking agents include cyclohexylcarbodiimide, ethyldimethylaminopropyl carbodiimide, N-ethylmorpholino cyclohexyl carbodiimide, diisopropyl carbodiimide.

It should be understood that the aforementioned vaccine can be in admixture with other proteins and these proteins include the proteins of known antigens or allergens. Thus when it is stated herein that the vaccine is characterized by the absence of an amino acid sequence corresponding to the entire protein antigen or allergen it is meant that notwithstanding the absence of the amino acid sequence of the entire protein antigen or allergen, the composition functions as a vaccine, i.e. provides protective immunization by formation of antibodies in the case of an antigen or a lessening of allergic sensitivity in the case of an allergen.

The composition of the aforementioned development is also useful for purposes other than as a vaccine. It is known, for instance, that certain patients suffering from hemophilia contain within their system an antibody to Factor VIII, Factor VIII being a substance which promotes clotting. It has long been an object to bind that Factor VIII antibody so that it, in turn, cannot interfere with any factor VIII which might be present in the blood stream. By determining the amino acid sequence of the Factor VIII protein, a synthetic antigenic composition can be prepared by the techniques described herein in which antigen compositions have H-epitopes corresponding to the anti-Factor VIII antibody. Such synthetic antigen compositions can be mono-specific to the anti-Factor VIII antibody. When introduced into the host hemophiliac, the H-epitopes in the synthetic antigenic composition are recognized by the anti-Factor VIII antibody with the result that they combine leaving the Factor VIII in the bloodstream free of the anti-Factor VIII antibody.

DEFINITIONS

Mono-specific antibody: an antibody that combines with a single antigen. A mono-specific antibody which is mono-specific to a single antigenic determinant combines only with that antigenic determinant (epitope).

Hetero-molecular antibody: an antibody that contains multiple different molecular forms of the same antibody.

Homo-molecular antibody: an antibody that contains only a single molecular form, i.e., each antibody molecule is the same as each other antibody molecule.

Monoclonal antibody: an antibody derived from a single cell line genetically identical and producing a homomolecular antibody.

SUMMARY OF THE INVENTION

In accordance with this invention there is provided an immunoglobulin consisting essentially of a mono-specific hetero-molecular antibody which is mono-specific to a single antigenic or allergenic determinant, i.e., the immunoglobulin being substantially free of antibodies to another antigen or allergenic determinant to the corresponding naturally occurring antigen or allergen or a different naturally occurring antigen or allergen. The antibody is specific to the H-epitope of a protein antigen or allergen. The H-epitope is defined by a sequence of at least six amino acids corresponding to the sequence of such amino acids in a protein antigen or allergen where the greatest local average hydrophilicity of the protein antigen or allergen is found. The local hydrophilicity of said protein antigen or allergen is defined and determined by:

A. assigning relative hydrophilicity values to the amino acids of the protein antigen or allergen in accordance with relative relationship of such amino acids as shown in the table below:

TABLE 1

| Amino Acid | Hydrophilicity Value |
| --- | --- |
| Arginine | 3.0 |
| Aspartic Acid | 3.0 ± 1 |
| Glutamic Acid | 3.0 ± 1 |
| Lysine | 3.0 |
| Serine | 0.3 |
| Asparagine | 0.2 |
| Glutamine | 0.2 |
| Glycine | 0.0 |
| Proline | −0.5 ± 1 |
| Threonine | −0.4 |
| Alanine | −0.5 |
| Histidine | −0.5 |
| Cysteine | −1.0 |
| Methionine | −1.3 |
| Valine | −1.5 |
| Isoleucine | −1.8 |
| Leucine | −1.8 |
| Tyrosine | −2.3 |
| Phenylalanine | −2.5 |
| Tryptophan | −3.4 |

B. determining the repetitive local average of hydrophilicity values at a plurality of points along the amino acid sequence, and C. determining from such local points of repetitive averages the points of greatest local average hydrophilicity.

Also in accordance with the present invention is a method of detecting in an amino acid chain a plurality of amino acid sequences each of which comprises at least six amino acids, each of which sequences corresponds to an antigenic or allergenic determinant including the H-epitope of a particular protein antigen or allergen. The method includes determining the points of relative greater local average hydrophilicity of the protein antigen or allergen by the following steps:

(1) assigning relative hydrophilicity values to the amino acids of the protein antigen or allergen in accordance with the relative relationship of such amino acids as shown in Table 1 hereinabove, (2) determining the repetitive local average of hydrophilicity values at a plurality of points along the amino acid chain, and (3) determining from such points of repetitive averages a plurality of points of relative greater local average hydrophilicity.

The present invention also concerns an improved diagnostic test kit comprising an antibody and a substance in a serum the presence of which is to be determined, the improvement wherein the antibody is a mono-specific antibody which is mono-specific to a single antigenic determinant. The mono-specific antibody is hetero-molecular. The antibody is specific to the H-epitope of a protein antigen or allergen. The H-epitope is defined by a sequence of at least six amino acids corresponding to the sequence of such amino acids in said protein antigen or allergen where the greatest local average hydrophilicity of the protein antigen or allergen is found. The local hydrophilicity of the protein antigen or allergen is determined by the following steps:

(1) assigning relative hydrophilicity values to the amino acids of the protein antigen or allergen in accordance with the relative relationship of such amino acids as shown in Table 1 herein, (2) determining the repetitive local average of hydrophilicity values at a plurality of points along the amino acid chain and (3) determining from such points of repetitive averages the points of greatest local average hydrophilicity.

This invention also relates to an improved process for the detection of an antigen by employing an antibody thereof, the improvement wherein the antibody is a mono-specific antibody which is mono-specific to a single antigenic determinant. The mono-specific antibody is hetero-molecular. The antibody is specific to the H-epitope of a protein antigen or allergen. The H-epitope defined by a sequence of at least six amino acids corresponding to the sequence of such amino acids in said protein antigen or allergen where the greatest local average hydrophilicity of the protein antigen or allergen is found. The local hydrophilicity of the protein antigen is determined by the steps (1) to (3) given above.

This invention also concerns a method of synthesizing a peptide residue containing a sequence of at least six amino acids corresponding to the sequence of such amino acids in a protein antigen or allergen where the greatest local average hydrophilicity of the protein antigen or allergen is found. The method involves determining the local hydrophilicity of the protein antigen or allergen as specified hereinabove and then arranging said sequence of at least six amino acids in the sequence corresponding to the points of greatest local average hydrophilicity. The above method would likewise apply to the synthesis of a peptide residue containing a sequence of at least six amino acids corresponding to the sequence of such amino acids in a protein antigen or allergen where the second greatest and third greatest local average hydrophilicity of the protein antigen or allergen is found.

DESCRIPTION OF SPECIFIC EMBODIMENTS

In the determination of the sequence of at least six amino acids which provide the H-epitope, it is preferred that more respective values than those set forth in Table 1 above be assigned to the respective amino acids in the protein antigen or allergen. Thus, there is set forth in Table 2 below the broad, preferred and most preferred ranges to be assigned for the determination of the at least six amino acids providing greatest local average hydrophilicity.

TABLE 2

| Amino Acid | Hydrophilicity Value | | |
|---|---|---|---|
| | Broad | Preferred | Most Preferred |
| Arginine | 3.0 | 3.0 | 3.0 |
| Aspartic Acid | 3.0 ± 1 | 3.0 ± .5 | 3.0 |
| Glutamic Acid | 3.0 ± 1 | 3.0 ± .5 | 3.0 |
| Lysine | 3.0 | 3.0 | 3.0 |
| Serine | 0.3 | 0.3 | 0.3 |
| Asparagine | 0.2 | 0.2 | 0.2 |
| Glutamine | 0.2 | 0.2 | 0.2 |
| Glycine | 0.0 | 0.0 | 0.0 |
| Proline | −.5 ± 1 | 0.0 ± .5 | 0.0 |
| Threonine | −0.4 | −0.4 | −0.4 |
| Alanine | −0.5 | −0.5 | −0.5 |
| Histidine | −0.5 | −0.5 | −0.5 |
| Cysteine | −1.0 | −1.0 | −1.0 |
| Methionine | −1.3 | −1.3 | −1.3 |
| Valine | −1.5 | −1.5 | −1.5 |
| Isoleucine | −1.8 | −1.8 | −1.8 |
| Leucine | −1.8 | −1.8 | −1.8 |
| Tyrosine | −2.3 | −2.3 | −2.3 |
| Phenylalanine | −2.5 | −2.5 | −2.5 |
| Tryptophan | −3.4 | −3.4 | −3.4 |

It will be recognized that these values are relative. By multiplying these values with a factor, one can obtain another set of values which can be similarly used to provide the same prediction and determination. The important concept is that the respective amino acids have the relative relationship as set forth in the table above. These arbitrary values are established for the purpose of providing a convenient means whereby the portion of a long chain protein molecule of highest hydrophilic characteristic is identified. When that is determined, the realization of the six amino acid accounting for that hydrophilicity peak is easily determined.

Thus, the procedure of the invention can be employed to determine the sequence of six amino acids of numerous unrelated antigens which provide the greatest hydrophilicity.

Specifically, the hepatitis B surface antigen has been studied to determine the sequence of six amino acids which determine the H-epitope. The sequence of amino acids for such antigen is as follows:

Lys Pro Thr Asp Gly Asn (which correspond to amino acids 141–146 of the hepatitis B surface antigen protein).

Similarly the sequence of amino acids for the human histocompatibility antigen HLA-B7 which determine the H-epitope is: Pro Arg Glu Glu Pro Arg (which correspond to amino acids 43–48 of the protein).

Similarly, the sequence of amino acids for the influenza hemagglutinin antigen (X31 strain) which determine the H-epitope is: Val Glu Arg Ser Lys Ala (which correspond to amino acids 105–110 of the protein).

The H-epitope for the A/memphis/102/72 strain of influenza hemagglutinin is: Lys Arg Gly Pro Asp Ser, corresponding to amino acids 140 to 145 of the protein.

The H-epitopes for two other strains of influenza hemagglutinin, A/Eng/878/69 and A/NT/60/68/29c, are identical to the H epitope of A/memphis/102/72 as stated above.

The H-epitopes of the A/NT/60/68 and A/Qu/7/70 strains of hemagglutinin are identical and comprise the following amino acids: Arg Asn Val Pro Glu Lys corresponding to to amino acids 321–326 of the proteins.

The H-epitope for the neuraminidase protein of the A/PR/8/34 strain of influenza is Arg Gly Arg Pro Lys Glu Lys, corresponding to amino acids 413 to 419 of the protein. This epitope contains seven amino acids because it comprises two adjacent and overlapping H epitopes of equal hydrophilicity, as is the case for the Japan strain hemagglutinin already described (in the original manuscript).

The H-epitope for the diphtheria toxin fragment A is: Glu Thr Arg Gly Lys Arg, corresponding to amino acids 168 to 173 of the protein.

The H-epitope for the avian sarcoma virus gp 37 protein is: Leu Arg Glu Ile Glu Arg Leu, corresponding to amino acids 37 to 43 of the protein (again, two adjacent and overlapping H epitopes yielding a seven amino acid sequence).

The H-epitope for the avian sarcoma virus src gene protein is: Lys Ser Lys Pro Lys Asp, corresponding to amino acids 5 to 10 of the protein.

The H-epitope for the E3/16 protein (external portion) of the adenovirus type 2 strain is: Lys Asp Lys Ile Gly Lys, corresponding to amino acids 40 to 45 of the protein.

The H-epitope for the Simian virus 40 VP1 protein is: Asp Asp Ser Pro Asp Lys Glu, corresponding to amino acids 77 to 83 of the protein (two adjacent and overlapping H epitopes).

The H-epitope for the available sequence of the fiber protein of adenovirus type 2 (N-terminal 80%) is: Asn Lys Asn Asp Asp Lys, corresponding to amino acids 393 to 398 of the protein.

The H-epitope of the Sindbis virus membrane glycoprotein E1 is: Ser Asp Arg Glu Gly Gln corresponding to amino acids 322 to 327.

The H-epitope of the Sindbis virus membrane glycoprotein E2 corresponds to the following amino acid chain: Asp Glu Ala Asp Asp Asn corresponding to amino acids 36 to 41.

The H-epitope for the Sindbis virus membrane glycoprotein E3 corresponds to amino acids 27 to 32 and has the following sequence: Thr Arg Glu Pro Ser Arg.

The H-epitope for the foot and mouth disease virus capsid protein VP1 corresponds to amino acids 179 to 184 and has the following amino acid sequence: Arg Met Lys Arg Ala Glu.

There are two sequences of amino acids for the influenza hemagglutinin antigen (Japan strain) which determine H-epitopes of equivalent hydrophilicity i.e., they provide identical local average hydrophilicity. They are Glu Lys Glu Asn Pro Arg (correspond to amino acids 96–101) and Lys Glu Asn Pro Arg Asp (correspond to amino acids 97–102). Similarly, the sequence of amino acids for the influenza hemagglutinin antigen (Victoria A strain) which determine the H-epitope is: Asn Asp Asn Ser Asp Lys (corresponding to amino acids 188–193).

Similarly, there are two sequences of amino acids for the Fowl Plague virus hemagglutinin antigen which determine H-epitopes of identical local average hydrophilicity. They are: Glu Arg Arg Glu Gly Asn (corresponding to amino acids 97–102) and Arg Arg Glu Gly Asn Asp (corresponding to amino acid 98–103).

Similarly, the sequence of amino acids for the human chorionic Gonadotropin B subunit antigen which determine the H-epitope is: Arg Arg Ser Thr Thr Asp corresponding to amino acids 94–99.

Similarly, the sequence of amino acids for the Human Beta-2 microglobulin antigen which determines the H-epitope is: Pro Thr Glu Lys Asp Glu which corresponds to amino acids 73–78.

Similarly, the sequence of amino acids for the human Myelin basic protein antigen which determines the H-epitope is: Gly Arg Asp Ser Arg Ser corresponding to amino acids 159–164.

Similarly, the sequence of amino acids for the Cholera Toxin B-chain antigen which determines the H-epitopes is: Glu Ala Lys Val Glu Lys corresponding to amino acids 79–84.

Another hepatitis B surface antigen has been studied to determine its sequence of six amino acids which determine the H-epitope. Its sequence is: Lys Pro Ser Asp Gly Asn corresponding to amino acid 141–146.

The sequence of amino acid for the E. Coli Heat Labile Toxin which determine the H-epitope is Glu Arg Met Lys Asp Thr corresponding to amino acids 66–71.

The sequence of amino acids for the E. Coli Heat Stabile Toxin provides two identical H-epitopes whose amino acid sequence is Asp Ser Ser Lys Glu Lys and Ser Glu Lys Lys Ser Glu corresponding to amino acids 26–31 and 46–51, respectively.

The ragweed allergen Ra3 has an H-epitope whose amino acid sequence is Cys Thr Lys Asp Gln Lys corresponding to amino acid 88–93.

The ragweed allergen Ra5 has an H-epitope whose amino acid sequence is Ser Lys Lys Cys Gly Lys corresponding to amino acids 40–45.

The streptococcial M protein (strain 24) has two identical H-epitopes whose amino acid sequences are
Arg Lys Ala Asp Leu Glu and
Lys Ala Asp Leu Glu Lys
corresponding to amino acids 58–63 and 59–64.

The trypanosoma brucei variant surface glycoprotein 117 has an H-epitope whose amino acid sequence is
Lys Ala Lys Glu Lys Gly
corresponding to amino acids 50–55.

In synthesizing peptides according to this invention, it is preferred to attach to the six amino acids which define the H-epitope at least three amino acids on either side thereof. These three amino acids can be the same acids in the same sequences as they occur in the natural protein. However, other acids can also be used. For instance, in the case of hepatitis Bs the amino acid sequence can be
Aba Aba Thr Lys Pro Thr Asp Gly Asn Aba Thr Aba
(Aba residues have replaced Cys residues).

The synthetic peptides can be prepared as follows:

1. Chemical Synthesis: The Merrifield solid phase procedure is used to build up the appropriate sequence of L-amino acids from the carboxyl terminal amino acid to the amino terminal amino acid. Starting with the appropriate carboxyl terminal amino acid attached to a polystyrene (or other appropriate) resin via chemical linkage to a chloromethyl group, benzhydrylamine group, or other reactive group of the resin, amino acids are added one by one using the following procedure for each:
   (a) Peptidyl resin is washed with methylene chloride
   (b) neutralized by mixing for 10 min. at room temperature with 5% (v/v) diisopropylethylamine (or other hindered base) in methylene chloride
   (c) washed with methylene chloride.
   (d) An amount of amino acid equal to six times the molar amount of the growing peptide chain is activated by combining it with one-half as many moles of a carbodiimide (e.g. dicyclohexylcarbodiimide, diisopropylcarbodiimide) for 10 minutes at 0° C., to form the symmetric anhydride of the amino acid. The amino acid used should be provided originally as the N-α-butyl-oxycarbonyl derivative, with side chains protected with benzyl esters (aspartic and glutarmic acids) benzyl ethers (eerine, threonine, cysteine, tyrosine), benzyl oxycarbonyl groups (lysine) or other protecting groups commonly used in peptide synthesis.

(e) the activated amino acid is reacted with the peptide resin for 2 hours at room temperature, resulting in addition of the new amino acid to the end of the growing peptide chain.

(f) The resin is washed with methylene chloride (g) The N-α-(butyloxycarbonyl)group is removed from the most recently added amino acid by reacting with 30% (v/v) trifluoroacetic acid in methylene chloride for 30 minutes at room temperature.

(h) The resin is washed with methylene chloride.

(i) Steps a through h are repeated until the required peptide sequence has been constructed. The peptide is then removed from the resin and simultaneously the side-chain protecting groups are removed, by reacting with anhydrous hydrofluoric acid containing 10% v/v of anisole. Subsequently, the peptide can be purified by gel filtration, ion exchange or high pressure liquid chromatography, or other suitable means.

In some cases, chemical synthesis can be carried out without the solid phase resin, in which case the synthetic reactions are performed entirely in solution. The reactions, and the final product, are otherwise essentially identical.

2. Isolation from natural sources: If sufficient quantities of the whole protein antigen are available, a limited portion of the molecule, bearing the H-epitope, may be excised by any of the following procedures:

(a) Digestion of the protein by proteolytic enzymes, especially those enzymes whose substrate specifically result in cleavage of the protein at sites immediately adjacent to the H epitope bearing sequence.

(b) Cleavage of the protein by chemical means. Particular bonds between amino acids can be cleaved by reaction with specific reagents. Examples include: bonds involving methionine are cleaved by cyanogen bromide; asparaginyl glycine bonds are cleaved by hydroxylamine; disulfide bonds between two cysteine residues are cleaved by reduction (e.g. with dithiothreitol).

(c) A combination of proteolytic and chemical changes.

It should also be possible to clone a small portion of the DNA that codes for the H epitope bearing peptide, resulting in the production of the peptide by bacteria.

The biologically derived H-epitope bearing peptide, once produced, may be purified by gel filtration, ion exchange or high pressure liquid chromatography, or other suitable means.

Analogously, one can form chains containing a plurality of H-epitopes of the same or different antigens or allergens by the following technique: An aqueous solution of the epitope bearing peptide or peptides is mixed with a water-soluble carbodiimide (e.g. ethyldimethylaminopropylcarbodiimide). This results in polymerization of the peptide(s); depending on the use of the side chain blocking groups mentioned above, either straight chain or branched polymers of the epitope bearing peptide can be made.

If desired the epitope containing chain employed in the present invention can have bonded thereto a chain of any the following moieties: polypeptide, polyaminoacid, polysaccharide, polyamide, polyacrylamide which can serve as a stabilizing chain or as a bridge between epitopes. Such chains are available commercially or, in the case of polyamino acids, are formed by a process which comprises: mixing a solution of epitope bearing peptide with a solution of the N-carboxylanhydride of the amino acid and allowing a base-catalyzed polymerization to occur, which is initiated by the amine groups of the peptide.

Although a carrier may not be required, if a carrier is employed the disposition of a chain or chains on a "carrier" can be effected as follows:

1. Protein Carrier: The protein and the H-epitope bearing peptide are dissolved together in water or other suitable solvent, and covalently linked via amide bonds formed through the action of a carbodiimide. The resulting product may contain one or more copies of the peptide per protein monomer.

2. Polysaccharide Carriers: Oligosaccharide carriers should have molecular weights in the range 1,000 to 1,000,000. In order to covalently link these to H-epitope peptides, suitable functional groups must first be attached to them. Carboxyl groups may be introduced by reacting with iodoacetic acid to yield carboxymethylated polysaccharides, or by reacting with carbonyldiimidazole to yield activated carbonyl esters. Carboxymethyl polysaccharides are coupled to the peptide by a carbodiimide reaction, while the activated carbonyl esters react spontaneously with peptides. Multiple copies of the H epitope bearubg peptide should be attached to each oligosaccharide unit.

3. Polyamino Acid Carriers: These carriers should have molecular weights in the range 1,000 to 1,000,000. Polylysine and polyornithine have primary amino groups on their side chains; polyaspartic acid and polyglutamic acid have carboxyl groups. Peptides may be coupled to these via amide bonds using the carbodiimide reaction. Another carrier that provides amino groups for coupling is polysine to which polyalanine has been attached to the side chains of the lysine residues. The H-eptitope bearing peptide may be attached to the ends of the polyalanine chains, also by a carbodiimide reaction. Multiple copies of the H-eptitope bearing peptide should be attached to each oligopeptide unit.

The respective epitope containing chains can be linked to one another by a cross-linking agent. Generally speaking, the cross-linking agent can be any one of a type identified above. Cross-linking is effected by reacting the epitope containing peptide residue with the cross-linking agent as follows:

Reaction with glutaraldehyde or a bis-imidate (e.g. dimethylsuberimidate) in aqueous solution results in polymerization of the epitope bearing peptide, with the cross-linking reagent forming covalent bridges between peptide monomers.

Antibodies generated in accordance with the present invention are present in immunoglobulins that are generated in accordance with the present invention in a titer of between 1:4 and 1:1,000,000, preferably between 1:100,000 and 1:1,000,000.

The immunoglobulin containing mono-specific antibodies of the present invention can serve as a source for diagnostic immunoglobulin to be used in serological testing, for example in identifying strain types of pathogenic organisms isolated from infected individuals.

By the use of radioimmunoassay or enzyme immunoassay, the present invention can be employed as a diagnostic tool for the detection of antibodies or antigens.

In order to more fully illustrate the nature of the invention and the manner of practicing the same, the following examples are presented:

EXAMPLE 1

A sequence of amino acids corresponding to a portion of the hepatitis B surface antigen protein was synthesized, having the following structure:

| 1 | 12 |
|---|---|
| Abc Aba Thr Lys Pro Thr Asp Gly Asn Aba Thr Aba | | of which the sequence Lys Pro Thr Asp Gly Asn corresponds to the H epitope, and the remaining amino acids are included to support the H epitope and to give it a proper 3-dimensional presentation for antigenicity.

Aba (amino butyric acid) residues have been included in place of cysteine residues that occur in the natural product, in order to preclude deleterious side reactions; no changes have been made in the six amino acids comprising the H epitope.

In order to assess the antigenic properties of this peptide, it was coupled to a polystyrene support (XE 305A resin beads, Rohm & Haas Co.). It wad linked covalently to the beads via a two amino acid (GlyGly) bridge between the carboxyl group of the twelfth amino acid (Aba) and an amino group (benzhydrylamine) of the polystyrene resin.

This peptide bearing resin was utilized in an immunological assay using reagents available commercially as the Aistria II assay (Abbott Laboratories), a commonly used diagnostic test for hepatitis B antigen. In this case the peptidyl resin was substituted for the polystyrene beads normally used in the test, and showed a clearly positive antigenic binding activity.

The peptide has subsequently been removed from the beads by treatment with hydrofluoric acid.

EXAMPLE 2

Determination of Antigenic Specificities in Polypeptide on Polystyrene Beads

To determine which antigenic specificities were present in a polypeptide prepared in accordance with this invention, the folloowing experiment was carried out:

Monospecific antibodies to the a,d, and y specificities of HBsAg (see Prince, A. M., Brotman, B., Ikram, H. in *Hepatitis and Blood Transfusion* (Vyas, G. N., Perkins, H. S., and Schmid, R. editors) Grune and Stratton, New York, 1972, Pp 147–154) were prepared, titered by passive hemagglutination and diluted to a titer of 1:2 to 1:4. In addition, anti-human serum albumin was titrated against albumin coated erythrocytes, and similarly diluted with 25 mg each of uncoated polystyrene beads, normal human serum (37° C. 30 min) coated beads, and beads with the attached polypeptide were washed twice with TAP buffer and then immersed in 200 μl diluted antibody. After 30 minutes at 37° C. and 1 hour ar 4° C., with shaking, the beads were removed by centrifugation (5000 rpm 10 min) and the antibody in the supernate was quantitated by passive hemagglutination against human type O red cells coated with HBsAg/ad by the chromic chloride method, similar cells coated with HBsAg/ay and human serum albumin and aldehyde fixed cells coated with HBsAG/ad.

The results, shown in Table A, reveal that the peptide coated bead, but not the two types of control beads, adsorbed anti-a and anti-d antibodies, but not anti-y. Furthermore, none of the beads non-specifically adsorbed anti-albumin.

It was concluded that the polypeptide treated contains HBsAg/a and HBsAg/d specificities but not HBsAg/y.

TABLE A

Adsorption of Antibody by HBsAg Peptide Coated Polystyrene Beads

Titer after adsorption vs.

| Beads | Antibody diluted to a titer of 1:2–1:4 | Chronic chloride coupled HBsAg/ad coated erythrocytes | Aldehyde fixed HBsAb/ad coated erythrocytes | Chronic chloride coupled HBsAg/ay coated erythrocytes | Aldehyde fixed human serum albumin coated erythrocytes |
|---|---|---|---|---|---|
| Control Human serum coated beads | Anti HBsAg/a | 1:4 | 1:2 | 1:2 | |
| | Anti HBsAg/d | 1:4 | 1:2 | — | |
| | Anti HBsAg/y | N.D. | N.D. | N.D. | |
| | Anti human serum albumin | | | | |
| Control uncoated beads | Anti HBsAg/a | 1:2 | N.D. | N.D. | |
| | Anti HBsAg/d | 1:2 | 1:4 | — | |
| | Anti HBsAg/y | — | — | 1:4 | |
| | Anti human serum albumin | | | | 1:4 |
| Hopp polypeptide coated beads | Anti HBsAg/a | — | — | — | |
| | Anti HBsAg/d | — | — | — | |
| | Anti HBsAg/y | — | — | 1.4 | |
| | Anti human serum albumin | | | | 1:4 |
| Antibody titer before adsorption tested at the same time | Anti HBsAg/a | 1:4 | 1:2 | 1:4 | |
| | Anti HBsAg/d | 1:4 | 1:2 | — | |
| | Anti HBsAg/y | — | — | 1:4 | |
| | Anti human serum albumin | | | | 4:4 |

[1]37° C. 30 min, 4° C. 1 hour, with shaking. Tested at the same time as adsorbed samples.

EXAMPLE 3

Polyglutamic Acid as a Carrier for H-Epitope Bearing Peptides

Experiments have been carried out to demonstrate the suitability of polyglutamic acid as a carrier for H-epitope bearing peptides. Linear poly ($\alpha$) glutamic acid with an average molecular weight of 21,000 was acetylated by adding 0.1 ml of acetic anhydride to a solution of 100 mg of polyglutamic acid in 1 ml of a 50% (vol/vol) solution of water and pyridine. A ninhydrin test demonstrated that acetylation of the terminal amino group was complete after 15 minutes. This acetylation prevents further polymerization of the polyglutamic acid during subsequent steps.

The γ carboxyl groups were activated by reacting with a five-fold molar ratio of ethyl, dimethyl amino propyl carbodiimide and a five-fold molar ratio of N-hydroxysuccinimide per 10 mg of acetylated polyglutamic acid dissolved in 0.5 ml of dimethyl sulfoxide. Complete esterification was achieved by 1 hr. at room temperature. The activated polyglutamic acid was precipitated and washed free of excess reagents by treating with three 5 ml washes of 0.1N HCl. The product was dried by evaporation and stored in a freezer until needed.

H-epitope peptides may be coupled to this polymer by dissolving 10 mg of activated polyglutamic acid, and 5 mg of the peptide, in 1 ml of dimethylsulfoxide containing 1% triethylamine. Under these conditions, 5 mg of the synthetic hepatitis peptide (p. 21, line 19 of original manuscript) could be completely coupled to 10 mg of polyglutamic acid in 15 minutes at room temperature.

Since the remaining activated carboxyls of the polyglutamic acid are not affected by the reaction, it is theoretically possible to subsequently add other amino compounds to the H peptide polymer. These compounds include other H peptides, adjuvants, and other molecules that affect the immunogenicity of the polymer.

Another modification that may affect the immunogenicity of the polymer, is to replace the N-terminal acetyl group with higher analogues, such as capryl, lauryl, or palmityl groups. These may enhance the immunogenicity directly, by acting as haptens, or may facilitate incorporation of the polymer into liposomes, a procedure known to enhance immunogenicity.

EXAMPLE 4

Generation of Antibodies

A synthetic peptide (sequence of amino acids) corresponding to a portion of the hepatitis B surface antigen protein synthesized according to Example 1 herein can be used for injection into animals, such as mice, to elicit immunoglobulin containing antibody according to the present invention.

Two synthetic peptide containing compositions, namely, H-peptide chemically associated with limpet hemocyanin (KLH-H) and H-peptide chemically associated with palmitic acid (HepK-FA) can be used.

The two formulations are absorbed to alum at pH 6.5. Chemical analysis would show that only 20% of the protein was adsorbed to the alum. These formations are put into the mouse potency test and the following results are reported:

(1) KLH-H gives one of 10 animals converting with a titer of 1:8 Ausab units.

(2) Hep K-FA gives one of 10 animals coverting with 292 Ausab units. 2-dose regimen; 56-day bleeding.

A single dose regimen with these two preparations gives no seroconversions.

The same two preparations are reformulated with alum at pH 5 at which pH greater than 80% of the protein is adsorbed. These preparations are also put into the mouse potency test with the following results:

(1) KLH-H gives 1 out of 4 animals converting with 1:8 Ausab units; single dose regimen; 28-day bleeding.

(2) Hep K-FA gives 0 of 7 animals converting; 2 dose regimen; 56-day bleeding.

A synthetic peptide as above, but coupled to an outer membrane protein from Group B meningococci using carbodiimide is utilized as above. The resulting conjugate is split in two and half of it, HPC-6 is held as an aqueous preparation and the other half, HPC-7 is adsorbed to alum with complete adsorption.

These preparations are run as both single dose and two dose regimens in the mouse potency test. No seroconversions are observed with either preparation in either regimen.

It is to be understood that the term "antigen" as used herein is intended to cover exo-antigens such as bacterial, viral, parasitic and plant antigens as well as autoantigens such as those responsible for such auto-immune diseases as Myasthenia Gravis and Auto Immune Thyroiditis, carditis and Nephritis.

GLOSSARY

| Amino Acid | Abbreviation |
|---|---|
| Arginine | Arg |
| Aspartic Acid | Asp |
| Glutomic Acid | Glu |
| Lysine | Lys |
| Serine | Ser |
| Asparagine | Asn |
| Glutamine | Gln |
| Glycine | Gly |
| Proline | Pro |
| Threonine | Thr |
| Alanine | Ala |
| Histidine | His |
| Cysteine | Cyr |
| Methionine | Met |
| Valine | Val |
| Isoleucine | Ile |
| Leucine | Leu |
| Tyrosine | Tyr |
| Phenylalanine | Phe |
| Tryptophan | Trp |
| Alpha-Aminobutyric Acid | Aba |

What is claimed is:

1. A method of synthesizing a peptide comprising a sequence of at least six amino acid residues corresponding to the antigenic or allergenic determinant on an antigenic or allergenic protein on the basis of hydrophilicity which method comprises:

(a) determining the amino acid sequence of said antigen or allergen;

(b) assigning relative hydrophilicity values to each sequenced amino acid on a basis selected as follows: arginine, 3.0; aspartic acid, 3.0±1.0; glutamic acid; 3.0±1.0; lysine, 3.0; serine, 0.3; asparagine, 0.2; glutamine 0.2; glycine, 0.0; proline −0.5±1.0; threonine, −0.4; alanine, −0.5; histidine, −0.5; cysteine −1.0; methionine, −1.3; valine, −1.5; isoleucine, −1.8; leucine, −1.8; tyrosine, −2.3; phenylalanine, −2.5; and tryptophan, −3.4;

(c) determining the repetitive local average of hydrophilicity values on the basis of said assigned values of each residue of at least six amino acids sequentially along said antigen or allergen;
(d) comparing said repetitive local averages and selecting the peptide of at least six amino acid residues corresponding to the greatest local average hydrophilicity;
(e) synthesizing a peptide comprising said selected peptide of at least six amino acid residues.

2. A method of synthesizing a peptide comprising a sequence of at least six amino acid residues corresponding to the antigenic or allergenic determinant on an antigenic or allergenic protein on the basis of hydrophilicity which method comprises:
(a) determining the amino acid sequence of said antigen or allergen;
(b) assigning relative hydrophilicity values to each sequenced amino acid on a basis selected as follows: arginine, 3.0; aspartic acid, 3.0±1.0; glutamic acid, 3.0±1.0; lysine, 3.0; serine, 0.3; asparagine, 0.2; glutamine 0.2; glycine, 0.0; proline −0.5±1.0; threonine, −0.4; alanine, −0.5; histidine, −0.5; cysteine, −1.0; methionine −1.3; valine, −1.5; isoleuine, −1.8; leucine, −1.8; tyrosine, −2.3; phenylalanine, −2.5; and tryptophan, −3.4;
(c) determining the repetitive local average of hydrophilicity values on the basis of said assigned valves of each residue of at least six amino acids sequentially along said antigen or allergen;
(d) comparing said repetitive local averages and selecting the peptide of at least six amino acid residues corresponding to the second greatest local average hydrophilicity;
(e) synthesizing a peptide comprising said selected peptide of at least six amino acid residues.

3. A method of synthesizing a peptide comprising a sequence of at least six amino acid residues corresponding to the antigenic or allergenic determinant on an antigenic or allergenic protein on the basis of hydrophilicity which method comprises:
(a) determining the amino acid sequence of said antigen or allergen;
(b) assigning relative hydrophilicity values to each sequenced amino acid on a basis selected as follows: arginine, 3.0; aspartic acid, 3.0±1.0; glutamic acid, 3.0±1.0; lysine, 3.0; serine, 0.3; asparagine, 0.2; glutamine 0.2; glycine, 0.0; proline −0.5±1.0; threonine, −0.4; alanine, −0.5; histidine, −0.5; cysteine −1.0; methionine −1.3; valine, −1.5; isoleucine, −1.8; leucine, −1.8; tyrosine, −2.3; phenylalanine, −2.5; and tryptophan, −3.4;
(c) determining the repetitive local average of hydrophilicity values on the basis of said assigned valves of each residue of at least six amino acids sequentially along said antigen or allergen;
(d) comparing said repetitive local averages and selecting the peptide of at least six amino acid residues corresponding to the third greatest local average hydrophilicity;
(e) synthesizing a peptide comprising said selected peptide of at least six amino acid residues.

4. A process according to claim 1 wherein the peptide so synthesized has up to 50 amino acids in the chain.

5. A process according to claim 2 wherein the peptide so synthesized has up to 50 amino acids in the chain.

6. A process according to claim 3 wherein the peptide so synthesized has up to 50 amino acids in the chain.

* * * * *

UNITED STATES PATENT AND TRADEMARK OFFICE
CERTIFICATE OF CORRECTION

PATENT NO. : 4,554,101

DATED : November 19, 1985

INVENTOR(S) : Thomas P. Hopp and Kenneth R. Woods

It is certified that error appears in the above-identified patent and that said Letters Patent is hereby corrected as shown below:

| | |
|---|---|
| Title Page, No. "[75] Inventor:" | After "Thomas P. Hopp, Seattle, Wash", insert --Kenneth R. Woods, Sea Cliff, New York -- |
| Title Page, under "U.S. Patent Documents" 5th line | Delete "12/1983" and substitute --11/1983-- |
| Col. 2, line 19 | Correct spelling of "Phenylalanine" |
| Col. 3, line 60 | Correct spelling of "hemagglutinin" |
| Col. 5, line 33 | Correct spelling of "Alternatively" |
| Col. 10, line 35 | Delete "acid" and substitute --acids-- |
| Col. 15, line 17 | Delete "Abc" under "1" and substitute --Aba-- |
| Col. 16, Table A, Line 2 | Above and in between "adsorption" and "vs." insert -- 1/ -- |
| Col. 16, Table A, line 9 under 5th column | Delete "1.4" and substitute --1:4-- |
| Col. 16, Table A, line 3 under last column | Delete "4:4" and substitute --1:4-- |
| Col. 19, line 25 | After "methionine" insert --,-- |

UNITED STATES PATENT AND TRADEMARK OFFICE
CERTIFICATE OF CORRECTION

PATENT NO. : 4,554,101

DATED : November 19, 1985

INVENTOR(S) : Thomas P. Hopp and Kenneth R. Woods

It is certified that error appears in the above-identified patent and that said Letters Patent is hereby corrected as shown below:

Col. 19, line 26      Delete "isoleuine" and substitute --isoleucine--

Signed and Sealed this

Eighteenth Day of March 1986

[SEAL]

Attest:

DONALD J. QUIGG

Attesting Officer

Commissioner of Patents and Trademarks